United States Patent [19]

Beavens et al.

[11] 3,961,901
[45] June 8, 1976

[54] ALKYLATION ACID END POINT DETECTOR

[75] Inventors: Charles R. Beavens, Port Arthur; Kenneth O. Higgs, Port Neches, both of Tex.

[73] Assignee: Texaco Inc., New York, N.Y.

[22] Filed: Dec. 23, 1974

[21] Appl. No.: 535,757

[52] U.S. Cl. ............................................ 23/253 R
[51] Int. Cl.² ........................................ G01N 31/16
[58] Field of Search ..................... 23/253 R, 259

[56] References Cited
UNITED STATES PATENTS

| | | | |
|---|---|---|---|
| 3,073,682 | 1/1963 | Lindsley | 23/253 R X |
| 3,625,655 | 12/1971 | Culp et al. | 23/253 R |

*Primary Examiner*—Robert M. Reese
*Attorney, Agent, or Firm*—T. H. Whaley; C. G. Ries; Henry C. Dearborn

[57] ABSTRACT

Alkylation-acid end point detector for measuring the titratable acidity of the acid. It employs an electrical titration cell to generate a potential that is related to the acidity pH of the acid. It amplifies and differentiates the potential followed by amplifying the first derivative signal to produce a sharp acid end point signal without using a second derivative.

7 Claims, 3 Drawing Figures

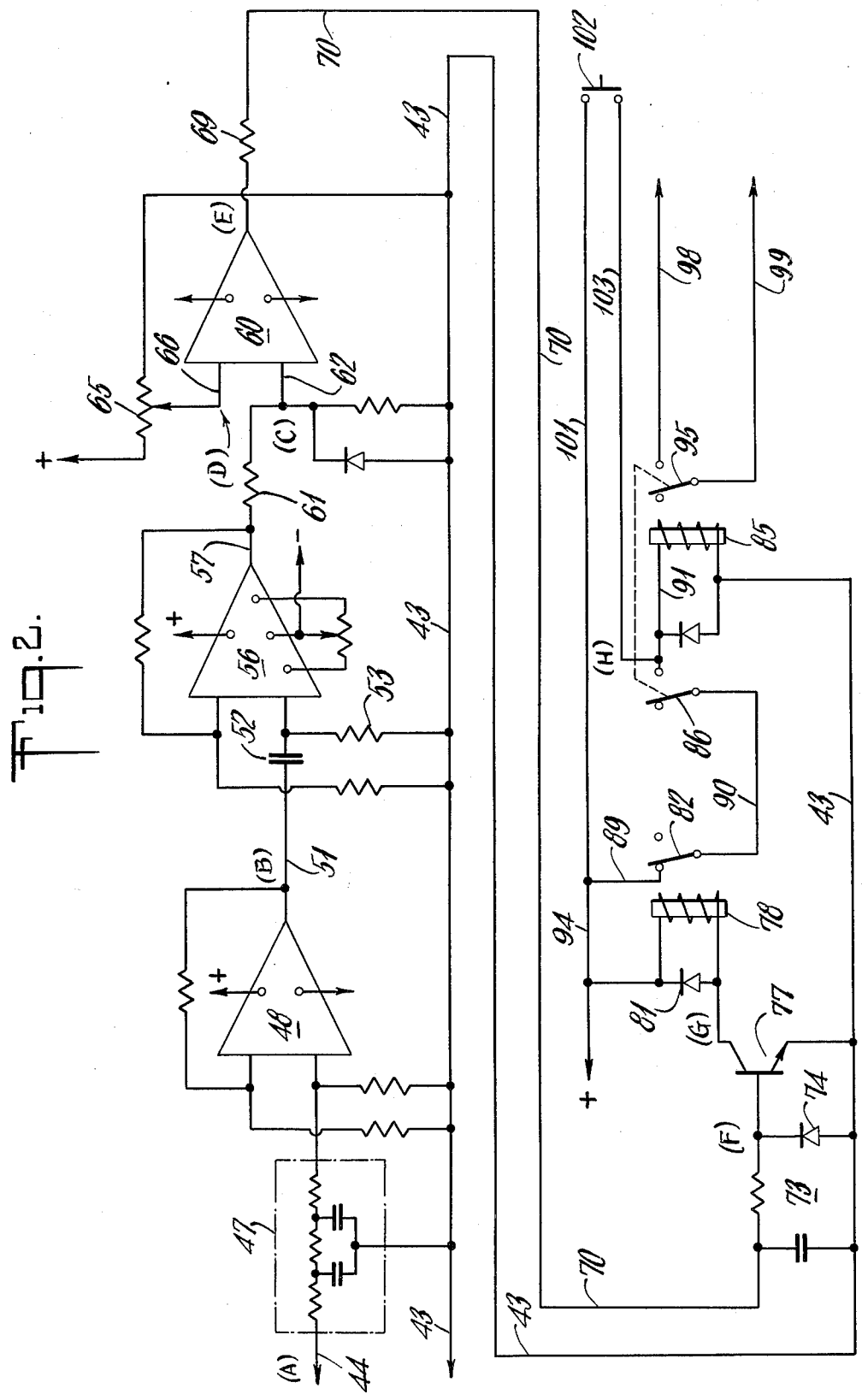

ALKYLATION ACID END POINT DETECTOR

BACKGROUND OF THE INVENTION

1. Field of the Invention

This invention concerns a titration end point detector, in general, and particularly deals with an alkylation acid end point detector that measures the titratable strength of the alkyation acid.

2. Description of the Prior Art

While instruments have been developed for measuring acid end points by carrying out automatic titration procedures, these have involved the use of second derivative signals as developed from an electrical titration cell. However, in order to develop such derivative signals it has been necessary to include the second derivative circuitry and consequently the sensitivity of the system becomes such that is very difficult to distinguish noise from the desired signal changes.

Consequently, it is an object of this invention to provide a simplified yet highly accurate and very reliable system for making alkylation acid end point measurements.

SUMMARY OF THE INVENTION

Briefly, the invention concerns an alkylation acid end point detector. Such detector comprises in combination an electrical cell for generating a potential that is related to the acidity pH of the alkyation acid, and an amplifier for increasing the amplitude of said potential. It also comprises means for differentiating said amplified potential in order to produce a first derivative signal from said potential, and means for amplifying said first derivative signal to produce a first acid end point signal.

Again briefly, the invention concerns an alkylation acid end point detector which comprises in combination an electrical cell for generating a potential that is proportional to the acidity pH of said alkylation acid. It also comprises an amplifier for increasing the amplitude of said potential, and means for differentiating said amplified potential in order to produce a first derivative signal from said potential. Also it comprises, means for amplifing said first derivative signal to produce a first acid end point signal, and a noise filter connected between said cell and said first named amplifier. In addition, it comprises voltage comparison means connected to said first derivative amplifying means for producing a second acid end point signal when said first acid end point signal has reached a predetermined amplitude and including means for adjusting said predetermined amplitude. It also comprises first relay means actuated by said second acid end point signal for marking the occurrence thereof, and a titrant solution, as well as a constant rate burette for introducing said titrant into said electrical cell. The said burette has motor means for actuating said titration, and the combination also comprises a second relay means having a latching circuit associated therewith, and a titration start switch, as well as circuit means including contacts on said second relay for energizing said burette motor to begin a titration. The combination also comprises a switch actuated by said first relay means, and said last named switch being connected into said latching circuit for deenergizing said second relay means whereby said latching circuit is opened and said burette motor is deenergized when said acid end point signal occurs.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 2 is a schematic circuit diagram illustrating the system that is employed for carrying out the end point determination according to this invention.

DESCRIPTION OF THE PREFERRED EMBODIMENT

Automatic titrators have been developed, but these have employed both first and second derivative arrangements for treating the signal that is created in the titration cell. Such arrangements have the drawback that the sensitivity is unduly great, particularly in regard to somewhat high frequency noise. Consequently, it is difficult to distinguish noise from the desired signal. However, it has been discovered that where the titrator is employed with alkylation procedures such that the titration is carried out on sulfuric acid, the end point signal developed by an electrical cell changes rapidly enough so that a first derivative system provides a sharp break output. Consequently, our invention may be employed and it will provide a reliable yet less expensive arrangement.

Figure 1:
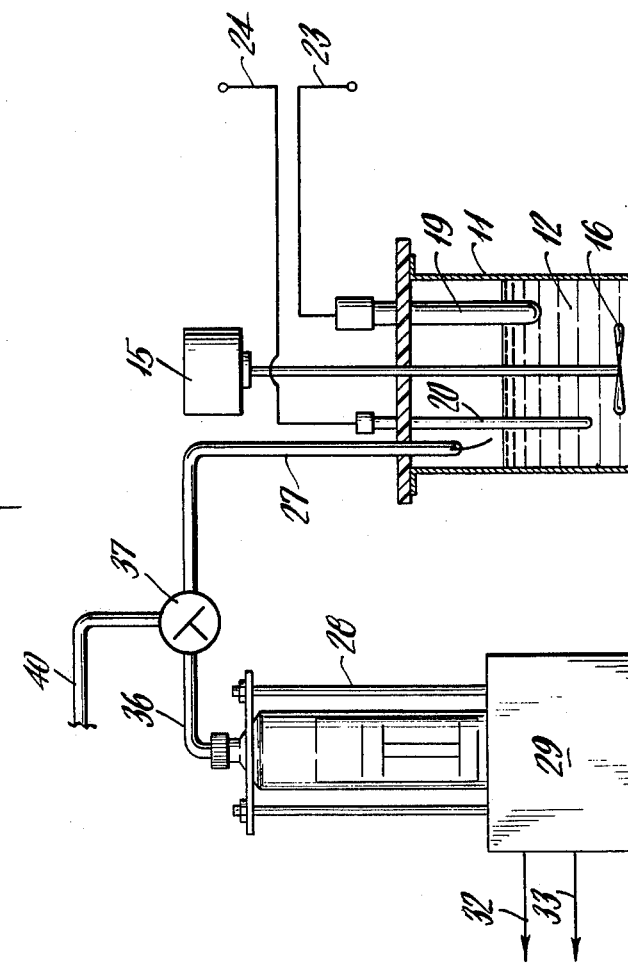
FIG. 1 is a schematic showing, illustrating a titration cell along with a constant rate burette that is associated therewith.

Referring to FIG. 1, there is shown an electrical titration cell 11 which contains a quantity of alkylation acid 12 that is to have its acidity measured. There is a stirring motor 15 that drives a paddle 16 for mixing the acid 12 during a titration run. The pH is measured by an electrical potential that develops between a reference electrode 19 and another electrode 20 that both extend into the acid solution 12.

The reference electrode is made of calomel while the other electrode is made of platinum-rhodium. These electrodes when immersed in the acid solution, will generate a negative and a relatively positive electrical potential on the respective circuit connection 23 and 24. This potential difference is related in amplitude to the acidity pH of the acid 12 in the cell 11.

In order to make an acidity measurement of the pH of the alkylation acid 12, there is introduced into the cell 11 a titrant such as sodium hydroxide. Such titrant is introduced through a delivery pipe 27 at a constant rate by having it delivered from a motorized burette 28. The burette is driven by a motor 29 which has an electrical control circuit connected to a pair of circuit wires 32 and 33. The titrant is pumped at a constant rate out from the burette and goes via a pipe 36 that is connected to the pipe 27 by means of a 3-way valve 37. The valve 37 also permits refilling of the burette 28 with titrant solution via a pipe 40, as necessary.

It will be understood that a titration procedure involves the introduction of titrant from the burette 28 at a constant rate, until the solution in the titration cell reaches the neutral state between acidity and basicity which is the end point of such titration determination. This end point will be indicated by the change in potential developed at the electrodes 19 and 20 and consequently the end point determination is related to the acidity pH of the solution.

FIG. 2 illustrates an electrical circuit according to this invention, which is employed for carrying out an end point determination. It has a common circuit connection 43 that has the electrode 20 connected to it via the circuit connection 24 (see FIG. 1). The reference electrode 19 is connected via its circuit connection 23 to an input circuit connection 44 of the FIG. 2 circuit.

The signal in the form of an electrical potential is developed at the reference electrode 19 and it is negative relative to the other electrode 20. However, this potential becomes less negative as the end point is reached during titration and consequently the circuit connections are made as indicated above with the reference electrode 19 connected directly to the input circuit connection 44 while the other electrode 20 is connected to the common circuit connection 43.

The signals go through a noise filter 47 and into one side of the input to an amplifier 48. The output of amplifier 48 goes over a circuit connection 51 where the signals are differentiated by means of a capacitor 52 and a resistor 53. The differentiated signals then go to the input of another amplifier 56. This produces an amplified sharp end point signal at its output, i.e. circuit connection 57. This end point signal goes to a voltage comparison amplifier 60 via a resistor 61 and an input circuit connection 62.

Voltage comparison amplifier 60 has a cut point adjustment potentiometer 65 connection to an other input circuit 66. The comparison amplifier 60 acts to produce a sharp change in output voltage when the cut point potential is reached. Such output signals goes via a resistor 69 and a circuit connection 70 to a current limiting and noise filtering network 73 that includes a diode 74 for clipping the negative portion of the sharp pulse signal arriving from the voltage comparator 60.

The pulse type end point signal controls the conductive state of a transistor 77 which in turn controls actuation of a relay 78. There is another diode 81 which absorbs the inductive kick when relay 78 is deenergized.

Actuation of the relay 78 controls the switching of a normally closed switch 82 that has its contacts in a holding circuit for another relay 85. The holding, or latching, circuit is associated with the relay 85 which has one set of normally open switch contacts 86 connected in series with the holding circuit. The holding circuit is conventional and includes circuit connections 89, 90, and 91. These connections go from the circuit for introducing a power supply to the system over a common connection 94 and to the coil of relay 85 which has the other end thereof connected to the common or ground circuit 43. Consequently, before the end-point is reached, and therefor when relay 78 has not yet been energized, there is a parallel holding circuit. This, of course, acts so that upon commencing any titration run, i.e. when relay 85 is energized, it will clamp or latch-in until the other relay 78 has been energized at the end-point.

Relay 85 also has another set of normally open contacts 95 which are connected into a control circuit for the burette motor 29 via connections 98 and 99. These connections lead to the connections 32 and 33 (see FIG. 1) for energizing the burette motor 29.

There is a start switch 102 that connects the power circuit 94 to one side of the relay 85 via connections 101 and 103. Switch 102 is spring biased open and it is only employed at the start of each titration run by momentarily closing and then releasing it.

Figure 3:
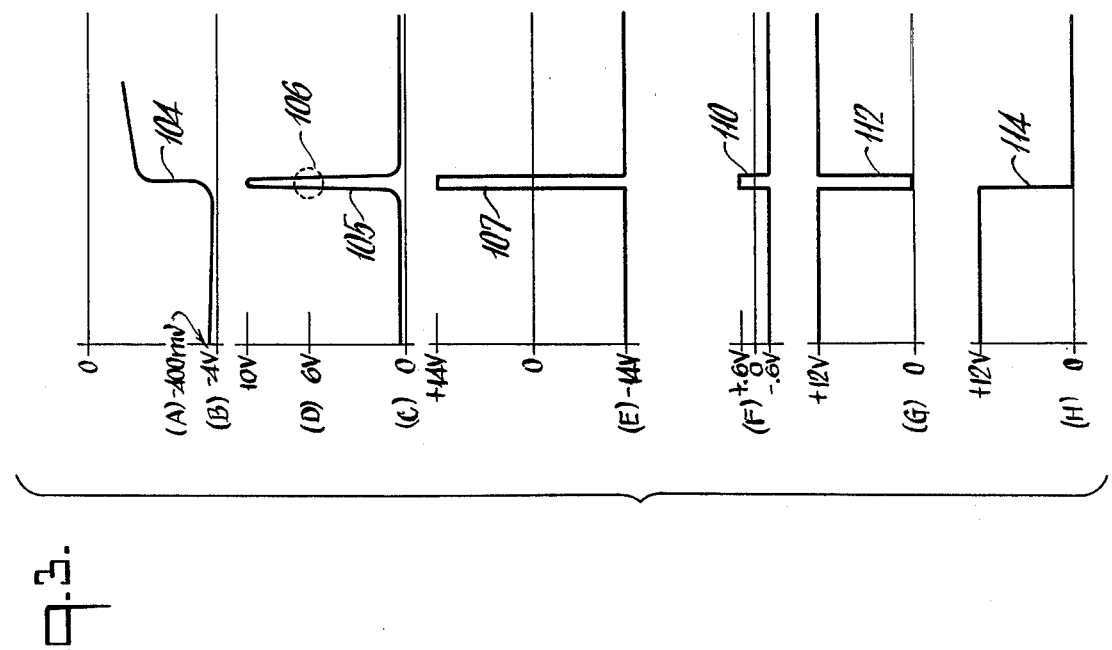
FIG. 3 is a series of wave form illustrations indicating the wave shape of signals at the corresponding locations on the FIG. 2 circuit.

FIG. 3 illustrates wave forms which represent the signals as they exist at the indicated locations throughout the FIG. 2 circuit, all at the time of the end-point detection. Thus, the potential that is developed at the electrode of the cell 11 is on the order of minus 400 millivolts at the input point (A) before the end-point is reached. Then after amplification by the amplifier 48, this same voltage is raised to minus 4 volts at circuit point (B) while the wave form remains substantially the same.

As the end-point is reached the potential rises quite rapidly which is indicated by a steep portion 104 on the first wave form. The signal is differentiated by the capacitor 52 and resistor 53 and amplified by the amplifier 56 so that its wave form appears at circuit point (C) as illustrated by the next curve. It will be observed that there is a sharp rising edge 105 which goes to a maximum voltage depending upon the circuit constants.

By setting the cut-off point potentiometer 65 at a predetermined amplitude, e.g. as indicated at the circuit point (D), the end point may be determined to be a given amplitude. For example, a desired amplitude is indicated by a circle 106 on the second wave form of FIG. 3. When that amplitude is reached, the output of comparator 60 is triggered and it creates a sharp pulse 107 at the circuit point (E). Pulse 107 makes the indicated full voltage swing which depends upon the circuit constants.

Circuit point (F) is illustrated by a wave form 110 which is the pulse 107 after it has passed through the network 73 and is applied to the base of transistor 77. The voltage at the collector, i.e. circuit point (G) drops to zero as illustrated by wave form 112, and the voltage applied to energize the relay 85 is cut-off as indicated by the wave form 114 which illustrates conditions at circuit point (H).

OPERATION

The operation of a titration run may be described as follows.

First the start switch 102 will be momentary depressed. This energizes relay 85 which closes its switch contacts 95 and 86. Switch 86 is in a series latching, or holding, circuit (as described above) and consequently will maintain relay 85 energized after the start switch 102 has been released.

The switch 95 closes the circuit including connections 98 and 99 which lead to circuit connections 32 and 33 so that the burette motor 29 is energized and a titration run is commenced. At this time, of course, the three way valve 37 will be in position to allow titrant to flow from the burette over pipe 36 and pipe 27 into the cell 11 so as to start neutralizing the acid solution 12.

During the run the electrical potential developed in cell 11 between the electrodes 19 and 20 will appear as an input signal on the circuit connection 44 of FIG. 2. It will be recalled that this circuit connection leads to the circuit wire 23 which is connected to the calomel electrode 19. The other electrode 20 is connected via its circuit connection 24 to the common circuit connection 43 of FIG. 2. Consequently, the electrical potentials being measured are negative on the circuit connection 44 relative to the common circuit 43.

It will be understood that the stirring motor 15 will have been energized before the start switch 102 was depressed, in order that the mixing will be continuous throughout the titration process.

The electrical potentials being developed by the titration cell 11 are being carried over the circuit connection 44 and are passed through the filter 47 before being connected to the amplifier 48. Amplifier 48 makes a straight amplification of the signal so that the potential is amplified from about minus 400 millivolts to about minus 4 volts.

Next the potential or signal voltage is differentiated by the capacitor 52 and resistor 53 as it is carried to the input of amplifier 56. Consequently, when the acidity pH of the solution 12 reaches a neutral state, the potential being developed at the electrodes rapidly changes toward zero. Such change is indicated by the portion 104 of the upper wave form in FIG. 3.

After differentiation of the signal, it becomes a very steep sharp rising signal as illustrated by the edge 105 of the next wave form on FIG. 3. Then the output signals from amplifier 56 go via resistor 61 to the input of the comparator 60 where the comparison potential will have been set at a desired amplitude by the adjustment of potentiometer 65. Consequently, when the predetermined voltage, e.g. 6 volts, has been reached by the output signal from amplifier 56 there will be a square wave pulse 107 developed by comparator 60. This pulse signal is carried via the resistor 69 and the circuit connection 70 to the network 73 which includes the diode 74. The current limited and noise filtered pulse, with any negative portion clipped, causes the transistor 77 to conduct. When transistor 77 conducts it energizes the relay 78, which is indicated by the wave form 112 of the FIG. 3 showings. This causes the switch 82 of relay 78 to be opened and thus it releases the latching circuit 90 of the other relay 85. Its actuation, of course, indicates the ending of the titration time and is the point at which the alkylation acid has been neutralized.

It will be appreciated that an end point detector according to this invention may be employed in an acid analyzer such as that shown and described in U.S. Pat. No. 3,625,655 to R. A. Culp, et al., issued Dec. 7, 1971 and assigned to the same assignee as this application. However, an end-point detector according to this invention provides for a simplified instrument which is consequently less expensive while at the same time being more reliable and better adapted for continuous use in a commercial process.

While a particular embodiment of the invention has been described above in considerable detail, in accordance with the applicable statutes, this is not to be taken as in any way limiting the invention but merely as being descriptive thereof.

We claim:

1. Alkylation acid end-point detector, comprising in combination,
   an electrical cell for generating a potential that is proportional to the acidity pH of said alkylation acid,
   an amplifier for increasing the amplitude of said potential,
   means connected to said amplifier for differentiating said amplified potential in order to produce a first derivative signal from said potential,
   means connected to said differentiator for amplifying said first derivative signal to produce a first acid end-point signal,
   a noise filter connected between said cell and said first named amplifier, and
   voltage comparison means connected to said first derivative amplifying means for producing a second acid end-point signal when said first acid end-point signal has reached a predetermined amplitude.

2. Alkylation acid end-point detector according to claim 1, wherein said voltage comparison means includes means for adjusting said predetermined amplitude.

3. Alkylation acid end-point detector according to claim 2, wherein the combination also comprises, first relay means actuated by said second acid end-point signal for marking the occurrence thereof.

4. Alkylation acid end-point detector according to claim 3, wherein the combination also comprises, a titrant solution, and
   a constant rate burette for introducing said titrant into said electrical cell,
   said burette having motor means for actuating said titration.

5. Alkylation acid end-point detector according to claim 4, wherein the combination also comprises,
   second relay means having a latching circuit associated therewith,
   a titration start switch, and
   circuit means controlled by said second relay for energizing said burette motor to begin a titration.

6. Alkylation acid end-point detector according to claim 5, wherein the combination also comprises,
   a switch actuated by said first relay means and connected into said latching circuit for deenergizing said second relay means and said burette motor when said acid end-point signal occurs.

7. Alkylation acid end-point detector, comprising in combination,
   an electrical cell for generating a potential that is proportional to the acidity pH of said alkylation acid,
   an amplifier for increasing the amplitude of said potential,
   means for differentiating said amplified potential in order to produce a first derivative signal from said potential,
   means for amplifying said first derivative signal to produce a first acid end-point signal,
   a noise filter connected between said cell and said first named amplifier,
   voltage comparison means connected to said first derivative amplifying means for producing a second acid end-point signal when said first acid end-point signal has reached a predetermined amplitude and including means for adjusting said predetermined amplitude,
   first relay means actuated by said second acid end-point signal for marking the occurrence thereof,
   a titrant solution,
   a constant rate burette for introducing said titrant into said electrical cell,
   said burette having motor means for actuating said titration,
   second relay means having a latching circuit associated therewith,
   a titrant start switch,
   circuit means including contacts on said second relay for energizing said burette motor to begin a titration,
   a switch actuated by said first relay means,
   said last named switch being connected into said latching circuit for deenergizing said second relay means whereby said latching circuit is opened and said burette motor is deenergized when said acid end-point signal occurs.

* * * * *